(12) United States Patent
Kumar et al.

(10) Patent No.: US 8,336,557 B2
(45) Date of Patent: Dec. 25, 2012

(54) SMOKELESS COMPRESSED TOBACCO PRODUCT FOR ORAL CONSUMPTION

(75) Inventors: Ashok Kumar, Richmond, VA (US); Carolina Marun, Midlothian, VA (US); Gregory J. Griscik, Midlothian, VA (US); David R. Golob, Richmond, VA (US); Jon Regrut, Richmond, VA (US); Suresh Shenoy, Richmond, VA (US); William R. Sweeney, Richmond, VA (US); Manuel Marquez-Sanchez, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 696 days.

(21) Appl. No.: 12/323,629

(22) Filed: Nov. 26, 2008
(Under 37 CFR 1.47)

(65) Prior Publication Data
US 2009/0293889 A1    Dec. 3, 2009

Related U.S. Application Data

(60) Provisional application No. 60/990,661, filed on Nov. 28, 2007, provisional application No. 61/059,626, filed on Jun. 6, 2008.

(51) Int. Cl.
*A24B 15/18* (2006.01)
(52) U.S. Cl. ........................... 131/111; 131/275
(58) Field of Classification Search .................. 131/111, 131/275
See application file for complete search history.

(56) References Cited

U.S. PATENT DOCUMENTS

| | | | |
|---|---|---|---|
| 4,298,012 A | 11/1981 | Wochnowski | |
| 4,366,824 A | 1/1983 | Rainer et al. | |
| 4,974,609 A | 12/1990 | Southwick et al. | |
| 2003/0070687 A1* | 4/2003 | Atchley et al. | 131/352 |
| 2003/0089883 A1* | 5/2003 | Knowlton et al. | 252/181.1 |
| 2003/0138384 A1* | 7/2003 | Stephenson et al. | 424/49 |
| 2004/0007687 A1* | 1/2004 | Dobbelstein et al. | 252/8.86 |
| 2005/0244521 A1 | 11/2005 | Strickland et al. | |
| 2006/0191548 A1 | 8/2006 | Strickland et al. | |
| 2008/0029117 A1 | 2/2008 | Mua et al. | |

FOREIGN PATENT DOCUMENTS

GB    2142822    1/1985

OTHER PUBLICATIONS

John C. Carter, "The Role of Lubricants in Solid Oral Dosage Manufacturing", Pharmaceutical Canada, 2001 vol. 2, No. 3.*
Homia.com.my, "Oil Palm Products", http://www.homia.com.my/catalog/allaboutpalm.htm.*

(Continued)

*Primary Examiner* — Matthew Daniels
*Assistant Examiner* — Cynthia Szewczyk
(74) *Attorney, Agent, or Firm* — Roberts Mlotkowski Safran & Cole, P.C.

(57) ABSTRACT

A consumable compressed tobacco product adapted to dissolve in an oral cavity. The compressed tobacco product is formed from a composition that includes at least one tobacco component, at least one flavorant, at least one filler-binder, at least one lubricant, at least one desiccant and at least one glidant. The compressed tobacco products are adapted to dissolve and provide tobacco satisfaction. A method of making a dissolvable compressed tobacco product is also provided.

36 Claims, 3 Drawing Sheets

OTHER PUBLICATIONS

Cabot Corporation, "Product Stewardship Summary: Treated Fumed and Colloidal Silica", http://www.cabot-corp.com/Downloads/DL201108181018AM67100/.*

"Cab-O-Sil Material Saftey Data Sheet", http://epoxy.com/msds/71.pdf.*

Khattab et al., "Effect of Mode of Incorporated of Disintegrants on the Characteristics of Fluid-bed Wet-granulated Tablest"; J. Pharm. Pharmacol, 1993, 45; pp. 687-691.

Lipps et al., "Characterization of Wet Granulation Process Parameters Using Response Surface Methodology. 1. Top-Spray Fluidized Bed"; Journal of Pharmaceutical Sciences / 937, vol. 83, No. 7, Jul. 1994; pp. 937-947.

Olmo et al., "Evaluation of Two Dextose-Based Directly Compressible Excipients"; Drug Development and Industrial Pharmacy, 24:8; pp. 771-778.

Parikh, et al., "Aqueous Ethylcellulose Dispersion of Ethylcellulose. I. Evaluation of Coating Process Variables", Pharmaceutical Research, vol. 10, No. 4, 1193; pp. 525-534.

Sastry and Khan, "Aqueous-Based Polymeric Dispersion: Face-Centered Cubic Design for the Development of Atenolol Gastrointestinal Therapeutic System", Pharmaceutical Development and Technology, 3(4), 1998; pp. 423-432.

* cited by examiner

SMOKELESS COMPRESSED TOBACCO PRODUCT FOR ORAL CONSUMPTION

RELATED APPLICATIONS

This patent application claims priority to the following provisional patent applications: Provisional Application Ser. No. 60/990,661, entitled "Smokeless Compressed Tobacco Product for Oral Consumption," filed on Nov. 28, 2007, and Provisional Application Ser. No. 61/059,626, entitled "Lipid Infused Smokeless Compressed Tobacco Product for Oral Consumption," filed on Jun. 6, 2008, each of which are hereby incorporated by reference in their entirety.

FIELD

This document relates generally to providing oral tobacco enjoyment through the use of a smokeless compressed tobacco product that includes a tobacco component.

Smokeless tobacco products, such as chewing tobacco and snuff, include an insoluble, residual component in an amount that typically requires disposal. Recently, other forms of smokeless tobacco products have entered the market place or have been described, including products in the form of gels, films and tablets.

Producing a smokeless tobacco product in a compressed form, such as a tablet, provides unique challenges. Conventionally, tablets may be classified as molded tablets or compressed tablets, each typically produced by a different method. Molded tablets may be manufactured by kneading an additive agent, such as a filler or binder, to form a mixture, adding a solvent such as water, ethanol or the like into the mixture to produce a moist powder, and forming the moist powder to have a predetermined shape by molding.

There are two methods of forming moist powder into tablets, one wherein the moist powder is forcibly pressed into a die having a certain shape, and the other wherein the moist powder is processed into a plate-like material by a rolling machine and a die of a certain shape is pressed against the material for punching. As may be appreciated, it can be difficult to deal with moist powder during manufacturing since, when the moist powder is pushed out of the die; it tends to stick to the surfaces, potentially causing a variation in product weight. Additionally, the surface may become rough, or the product may become broken as its mechanical strength is compromised.

Compressed tablets can be molded from dry powder at relatively high pressures. By applying force to the material, the powder granules are pressurized and instantaneously formed into a tablet. While compressed tablets are more suitable for mass production and can be superior to their molded counterparts, with respect to accuracy and quality, since the dry powder is compressed at high pressure, the compressed product can potentially be inferior with respect to solubility and disintegration. These issues can be particularly acute when seeking to form a compressed tobacco product capable of providing tobacco enjoyment. For example, when working with tobacco, moisture content can become an issue and, as such, must be controlled throughout the entire process.

As such, there remains a need for a dissolvable smokeless tobacco product that provides tobacco enjoyment.

SUMMARY

Disclosed herein are dissolvable compressed tobacco products for oral consumption and methods for making compressed tobacco products.

In one form, the tobacco component may include finely ground particles of a blend of tobaccos, including blends comprising Bright, Burley. Dark Air Cured or Oriental tobaccos and other blend components, such as ground improved stem, and also including traditional tobacco flavors and/or tobacco flavor enhancers such as those found in cigarettes. In one form, the tobacco component may comprise up to 100 percent improved stem. In another form, the tobacco component may comprise 100 percent improved bright stem.

In another form, the tobacco component may instead include individual tobacco blend components, such as the natural tobaccos, reconstituted tobacco sheet, and/or tobacco substitutes of natural or synthetic origin. A single variety of the aforementioned tobaccos may be used instead of a blend. The tobacco may be cured or uncured; however, cured tobacco is preferred.

The tobacco component may include ground or powdered tobacco laminae and/or stem (e.g., tobacco fines) having an average particle size of less than about 1 mm (e.g., less than about 0.5 mm or less than about 0.1 mm). Further, the average particle size may be greater than about 100 nanometers or greater than about 1 micron.

In a further form, the compressed tobacco product is infused with at least one lipid.

In a further form, the binder can comprise pullulan, cellulose ethers, sodium alginate, pectin, gums, starches, sugar alcohols, sodium carbonate, calcium carbonate, potassium carbonate, maltodextrin, and mixtures thereof.

In a still further form, the tobacco component includes a ground or powdered tobacco (e.g., ground or powdered laminae and/or stem) and/or a tobacco extract. The tobacco component may be made from a cured tobacco.

In one form, the ground or powdered tobacco has an average particle size of between about 100 nm and 1 mm. For example, the tobacco component can have a particle size of about 60 mesh or finer. In another form, the particle size is 120 to 400 mesh or 300 to 400 mesh.

The tobacco component can be incorporated within the compressed tobacco product.

The compressed tobacco product can comprise one or more optional additives such as flavorants, sweeteners, fragrances, coloring agents, filling agents and preservatives.

In another form the compressed tobacco product is both dissolvable and spitless or disintegratable in saliva.

These and other features will be apparent from the detailed description taken with reference to the accompanying drawings.

BRIEF DESCRIPTION OF THE DRAWINGS

Further explanation may be achieved by reference to the description that follows and the drawings illustrating, by way of non-limiting examples, various forms, wherein.

DETAILED DESCRIPTION

Figure 1A:
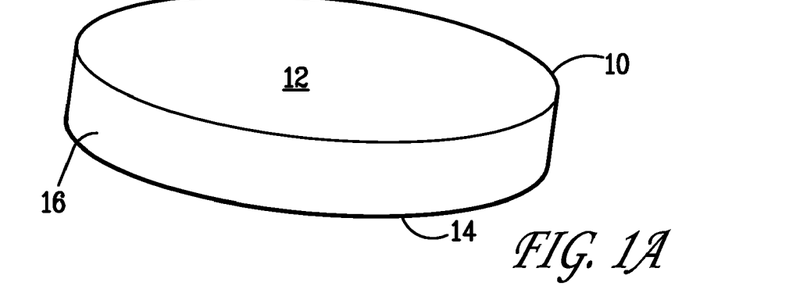
FIG. 1A is a perspective view of a compressed tobacco product in the form of a circular tablet.

Various aspects will now be described with reference to specific forms selected for purposes of illustration. It will be appreciated that the spirit and scope of the products, compositions and methods disclosed herein are not limited to the selected forms. Moreover, it is to be noted that the figures provided herein are not drawn to any particular proportion or scale, and that many variations can be made to the illustrated forms. Reference is now made to FIGS. 1A-2, wherein like numerals are used to designate like elements throughout.

DEFINITIONS

The term "coating" refers to any material or composition added or applied to the compressed tobacco product. For example, in one form, a coating may be added to the compressed tobacco product by spraying the compressed tobacco product with an aqueous or non-aqueous dispersion.

The term "colorant" as used herein incorporates the common usage of the term and refers to any composition that adds color to a formulation.

The terms "compressing," "pressing," "molding" and "press molding" refer to the process of applying compressive force to a formulation (powder or granules), as within a die, to form a compressed tobacco product.

The term "drying" and "dried" refer to a process which decreases the water content of a composition. For example, in one form, the composition is manufactured into a compressed tobacco product using a granulation process and dried after its initial granulation and compression into a tablet form. In another form, the compressed tobacco products are coated with an aqueous dispersion, which is subsequently dried.

The term "dry weight" as used herein incorporates the common usage of the term and, in the context of the compressed tobacco products disclosed herein, means the weight of a compressed tobacco product after substantially all of the water (or other solution or solvent) has been removed.

The term "formulation" refers to any mixture of compositions used to make the compressed tobacco products disclosed herein.

The term "disintegrant" as used herein incorporates the common usage of the term and refers to any composition which decreases the disintegration time (accelerates the rate of disintegration) of a compressed tobacco product.

The term "filler" as used herein incorporates the common usage of the term and refers to any inert material or composition added to a formulation to add bulk.

The term "flavorant" as used herein incorporates the common usage of the term and refers to any composition which adds flavor to a formulation.

The term "granulating" refers to the process of blending and mixing a formulation. Granulation may be conducted using a dry process or in an aqueous solution (wet granulation).

The term "incorporated in" means that a component (e.g., a tobacco component or other component) can be mixed with other components used to form a compressed tobacco product and/or added to (e.g., sprayed on, printed on, dusted on, etc.) a compressed tobacco product as a coating or layer during or after formation.

The term "slip melting point" is defined as the temperature at which a column of fat in an open capillary tube moves up the tube when it is subjected to controlled heating in a water bath. Because of their polymorphic behavior, the slip point of some fats is dependent on the previous treatment of the sample.

The term "sweetener" as used herein incorporates the common usage of the term and refers to any composition that sweetens the taste of a formulation.

The term "tablet" is used in its common context, and refers to a solid composition made by compressing and/or molding a mixture of compositions in a form convenient for buccal application.

Referring to FIG. 1A, an exemplary dissolvable compressed tobacco product 10 is shown that is adapted to be consumed orally and formed from a composition that includes at least one tobacco component, at least one flavorant, at least one sweetener, at least one filler-binder, at least one lubricant; at least one desiccant and a glidant. In one form, the compressed tobacco product is infused with at least one lipid. Other optional components may be employed, as will be described hereinbelow. Compressed tobacco product 10 includes at least a first surface 12, a second surface 14 and a side surface 16. One or more of these surfaces may optionally be coated, treated, embossed or debossed, as will also be described hereinbelow.

In one form, the composition used to make compressed tobacco product includes one or more tobacco components and may include finely ground particles of a blend of tobaccos, including blends comprising Bright, Burley, Dark Air Cured or Oriental tobaccos and other blend components, such as ground improved stem, reconstituted tobacco sheet and/or tobacco substitutes. Non-cigarette tobaccos such as *N. Rustica* are also contemplated for use herein. Traditional tobacco flavors and/or tobacco flavor enhancers, such as those found in cigarettes, may be optionally employed. In one form, the composition used to make compressed tobacco product may include ground improved stem, as described in U.S. Pat. No. 4,298,012, the contents of which are hereby incorporated by reference in their entirety. In another form, the composition may include ground improved stem, as described in U.S. Pat. No. 4,366,824, the contents of which are hereby incorporated by reference in their entirety, or ground improved stem produced in accordance with other methods known to those skilled in the art, or blends thereof.

In one form, the tobacco component may comprise up to 100 percent improved stem. In another form, the tobacco component may comprise 100 percent improved bright stem.

In another form, the tobacco component may instead include an individual tobacco blend component, such as Bright, Burley, Dark Air Cured or Oriental tobacco. As indicated above, non-cigarette tobaccos such as *N. Rustica* are also contemplated for use herein. The tobacco may be cured or uncured; however, cured tobacco is preferred.

The tobacco component may include ground or powdered tobacco laminae and/or stem (e.g., tobacco fines) having an average particle size of less than about 1 mm or less than about 0.5 mm or less than about 0.1 mm. Further, the average particle size may be greater than about 100 nanometers or greater than about 1 micron. In one form, average particle size may be between about 1 micron and about 0.1 mm (e.g., 400 mesh tobacco dust, wherein about 85 to about 95% of the particles pass through a mesh of 400 wires per square inch).

The tobacco component may be aged, cured, dried and shredded or ground before the tobacco is incorporated into a compressed tobacco product. Also the tobacco component may include mixtures of ground and shredded tobacco. Optionally, the tobacco component may comprise shredded, ground and/or powdered expanded tobacco. In one form, water content may be controlled to between about 2 to about 10 percent. The tobacco particles may also include one or more binders, which agglomerate smaller particles of tobacco together, and which may also hold fillers, flavorants, lipids and other additives, which adhere to the tobacco particles. Binders suitable for agglomerating tobacco particles together include those described herein as suitable for use in forming the compressed tobacco product.

The exemplary compressed tobacco product includes a tobacco component in an amount effective to impart a desired tobacco flavor to the compressed tobacco product. In another form, the amount of tobacco component is effective to provide tobacco satisfaction. Thus, the amount per compressed tobacco product of one or more tobacco components can be selected as a function of, for example, the desired flavor impact, the flavor desired and/or other desired organoleptic effects. By way of example, the compressed tobacco product may include from about 20% to about 70% by weight of one or more tobacco components or from about 30% to about 50% or about 40% by weight of one or more tobacco components, based on the final formulation.

In one form, the compressed tobacco product may include about 30% to about 50% by weight tobacco components, the tobacco components including about 10% to about 20% by weight Dark Air Cured tobacco and about 80% to about 90% by weight ground improved stem. In another form, the tobacco components include about 15% by weight Dark Air Cured tobacco and about 85% by weight ground improved stem.

The compressed tobacco product may also include a filler-binder which may comprise microcrystalline cellulose, sprayed processed lactose, dicalcium phosphate dehydrate, sprayed processed sucrose, pre-gelatinized starch or mixtures thereto. The use of such a filler-binder or a combination of one or more of the afore-mentioned filler-binders may be employed in an overall formulation to achieve a target performance, i.e. to increase disintegration time, maintaining integrity of the compressed tobacco product and/or achieve appropriate hardness and friability characteristics.

In one form, microcrystalline cellulose is employed. The microcrystalline cellulose may be Avicel® colloidal microcrystalline cellulose, obtained from FMC Corporation of Philadelphia, Pa. Microcrystalline cellulose can benefit mouth feel and provide fat-like properties. It also imparts emulsion stability, opacity and suspension.

The compressed tobacco product may also include one or more lipids. Lipids may be broadly defined as fat-soluble, naturally-occurring molecules and include fats, oils, waxes, cholesterol, sterols, fat-soluble vitamins, monoglycerides, diglycerides, triglycerides, phospholipids, and the like. Lipids also encompass molecules such as fatty acids and their derivatives, as well as other sterol-containing metabolites, such as cholesterol. Lipids may be broadly defined as hydrophobic or amphiphilic small molecules and may be divided into the following categories: fatty acyls, glycerolipids, glycerophospholipids, sphingolipids, saccharolipids and polyketides, sterol lipids and prenol lipids.

In one form, the compressed tobacco product includes one or more lipids selected from tropical oils and butters, vegetable oils, shortenings and non-nutritive synthetics, such as sucrose polyesters. In one form, the synthetic is Olean® brand olestra, available from the Procter and Gamble Company of Cincinnati, Ohio.

In one form, the compressed tobacco product includes palm oil and/or other tropical oils such as coconut oil. Palm oil is a lauric-type oil that is a solid fat at room temperature and water-like in appearance when melted. Palm kernel oil is known to be one of the cleanest tasting vegetable oils. Palm oil possesses the advantages of high stability, is resistant to oxidation and has a good texture. In one form, the palm oil is palm kernel oil that has been refined, bleached, hydrogenated, and deodorized. In one form, the palm kernel oil is grade P-100, having a slip melting point of about 96 to about 104° F. Slip temperatures can be modified by the addition of tropical oils with higher oleic and/or stearic acid content or by the addition of stearate salts and/or esters Other ingredients that may be used as well include, but are not limited to, gum acacia or gum arabic, xanthan gum, guar gum, gum tragacanth, gum karaya, carrageenan, locus bean, pectin, sodium alginate, methyl cellulose, carboxymethyl cellulose, corn syrup, gelatin, maltodextrin, and starches.

The use of maltodextrin as a filler-binder has several advantages when used in the compressed tobacco products disclosed herein. Maltodextrin improves product texture, improves product hardness and provides a better mouth feel for consumers. It also is a good granulation agent. Maltodextrin is a moderately sweet polysaccharide frequently used as a food additive. It is produced from starch and is usually produced as a creamy white hygroscopic powder. Maltodextrin is easily digestible, being absorbed as rapidly as glucose. Maltodextrin can be derived from any starch. In the U.S., this starch is usually corn or potato, whereas, elsewhere (e.g. Europe), it is commonly wheat.

Lubricants can aid in the manufacturing of a compressed tobacco product and assist in reducing or preventing ejection sticking of the compressed tobacco product formulation to the pressing dies and punches. Ejection sticking can be a problem when a formulation comprising a tobacco component is pressed into tablets by a dry blend process. This difficulty may be overcome by the use of an insoluble lubricant such as magnesium stearate, calcium stearate or derivatives thereof. The insoluble lubricant can be present in an amount between about 0.1% and about 8.0%, or between about 0.5% and about 5.0%, of the dry weight of the compressed tobacco product.

In another form, the compressed tobacco product disclosed herein can include other lubricants, such as fatty acids, an example of which is stearic acid. The fatty acid may be present in the compressed tobacco product in an amount between about 0.1% and about 8.0%, or between about 0.5% and about 5.0%, of the dry weight of the compressed tobacco product.

In yet another form, the compressed tobacco product disclosed herein can include a hydrophilic lubricant, such as by way of example but not of limitation, DL leucine, sodium benzoate, polyethylene glycol or mixtures thereof. The hydrophilic lubricant may be present in the compressed tobacco product in an amount between about 0.1% and about 8.0%, or between about 0.5% and about 5.0%, of the dry weight of the compressed tobacco product.

In still yet another form, the compressed tobacco product can include talc as a lubricant in an amount between about 0.1% and about 8.0%, or between about 0.5% and about 5.0%, of the dry weight of the compressed tobacco product.

In one form, disintegrants may also be included in the compressed tobacco products disclosed herein. For example, non-saccharide water soluble polymers such as crosslinked polyvinylpyrrolidone, available under the trademark Kollidon® from BASF USA of Florham Park, N.J., and crosslinked acrylic acid-based polymers, available under the trademark Carbopol®, from Lubrizol Corporation of Wickliffe, Ohio, can be added to the formulation to further enhance the rate of disintegration. Other disintegrants that can be used include, for example, but not by way of limitation, croscarmellose sodium, sodium starch glycolate, and the like; see, e.g., Khattab (1992) *J. Pharm. Pharmacol.* 45:687-691. When employed, sodium starch glycolate may be present in an amount of between about 4% to about 6%; crosslinked polyvinylpyrrolidone, such as crospovidone, may be present in an amount of between about 2 to about 4%; and modified cellulose, such as croscarmellose sodium, may be present in an amount of between about 1 to about 4%, of the dry weight of the compressed tobacco product. When starches or pre-gelatinized starches, such as rice starches are employed, they may be present in an amount from about 5% to about 15%, of the dry weight of the compressed tobacco product.

In another form, ingredients that perform the multiple functions of a binder, disintegrant, flow-aid and lubricant may be added to the formulation. A partially pre-gelatinized maize starch, available under the trademark Starch 1500® from Colorcon, Inc. of West Point, Pa., is an example of such a material.

In yet another form, one or more glidants may be added to enhance the flowability of the compressed tobacco product formulation. Materials having glidant functionality include, by way of example, but not of limitation, calcium silicate, magnesium stearate, calcium stearate, zinc stearate, starch, magnesium lauryl sulfate and silica aerogels, such as fumed colloidal silica. Having particular utility in the compressed tobacco products disclosed herein are the fumed colloidal silica such as those available under the trademark Cab-O-Sil® from Cabot Corporation of Billerica, Mass. When employed, fumed colloidal silica may be used at a concentration of less than about 2% or between about 0.25% to about 0.5% of the dry weight of the compressed tobacco product. When excessive adhesion to punch faces is encountered, higher concentrations may be employed.

In still yet another form, a desiccant may be added to control product dryness. Materials having desiccant functionality include, by way of example, but not of limitation, anhydrated nystose, silicon dioxide, magnesium sulfate and silica aerogels, such as fumed colloidal silica. In one form, fumed colloidal silica, such as those available under the trademark Cab-O-Sil® from Cabot Corporation of Billerica, Mass., may be used. When employed, fumed colloidal silica may be used at a concentration of less than about 1% or between about 0.25% to about 0.5% of the dry weight of the compressed tobacco product.

In one form, fumed colloidal silica may serve as a multi-functional component of the compressed tobacco products disclosed herein. As indicated above, the use of fumed colloidal silica can provide dissicant and glidant functionalities to the compressed tobacco product. Additionally, it can provide lubricant functionality in the formation of the compressed tobacco products disclosed herein.

The compressed tobacco products may further comprise optional components that may be added in effective amounts to control the organoleptic, aesthetic and/or mechanical properties of the films. Optional additives include, but are not limited to, additional flavorants, sweeteners, fragrances, colorants, preservatives, salts and the like.

Flavorants that may be employed in the compressed tobacco products disclosed herein include those described in commonly-owned U.S. Pat. No. 4,974,609, hereby incorporated by reference in its entirety for all that it discloses. For example, suitable tobacco flavorants include, but are not limited to, flavoring agents blended with tobacco, tobacco substitutes, or a mixture thereof. Exemplary natural and artificial flavorants include, but are not limited to, peppermint, spearmint, wintergreen, menthol, cinnamon, chocolate, vanillin, licorice, clove, anise, sandalwood, geranium, rose oil, vanilla, lemon oil, cassia, fennel, ginger, ethylacetate, isoamylacetate, propylisobutyrate, isobutylbutyrate, ethylbutyrate, ethylvalerate, benzylformate, limonene, cymene, pinene, linalool, geraniol, citronellol, citral, orange oil, coriander oil, borneol, fruit extract, and the like. In one form, additional flavor and aroma agents are essential oils, naturally ground coffee, tea, cacao, and mint and essences of coffee, tea, cacao, and mint. The flavorants can be added in encapsulated or non-encapsulated form. When encapsulated, flavor release control may be used to achieve a desired sensorial experience.

The exemplary compressed tobacco products may optionally comprise both natural and artificial sweeteners. Exemplary sweeteners include water soluble sweeteners such as monosaccharides, disaccharides and polysaccharides (e.g., xylose, ribose, sucrose, maltose, fructose, glucose, maltose, and mannose). Other sweeteners that may be employed are altern, aspartame and those marketed under the trademarks, SucraSweet™ and Nutrinova®. In addition, or in the alternative to sweeteners, the exemplary compressed tobacco products can comprise souring agents such as acetic acid, adipic acid, citric acid, lactic acid, malic acid, succinic acid, tartaric acid, and mixtures thereof.

Exemplary compressed tobacco products can also include colorants in an amount sufficient to impart a desired color to a compressed tobacco product. Colorants can be incorporated into the mixture of components used to form the compressed tobacco products and/or coloring agents can be applied to (e.g., sprayed on or printed on) one or more surfaces of a compressed tobacco product. Colorants can be incorporated into the compressed tobacco products in an effective amount up to about 5% by weight of the final, compressed tobacco product, or up to about 2% by weight.

Additional fillers can be used to control the compressed tobacco product's physical properties (e.g., texture, weight, etc.). Exemplary fillers include, but are not limited to, cellulose, titanium oxide, magnesium silicate (e.g., talc), aluminum silicate, magnesium carbonate, calcium carbonate (e.g., limestone), calcium phosphate, calcium sulfate, zinc oxide, aluminum oxide, and mixtures thereof. When employed at a concentration of about 0.1 to about 2.0%, titanium oxide may serve as an excellent whitening agent. Bentonite or other white clays can also be used as colorants, either in fillers or as coatings. Polyphosphates, such as sodium hexametaphosphate, can also be used as fillers or in coatings.

Exemplary compressed tobacco products can also optionally include preservatives. Exemplary preservatives include, but are not limited to, acetic acid, benzoic acid, citric acid, lactic acid, malic acid, sorbic acid and tartaric acid. The salts of organic acids can also be used such benzoates and sorbates. One or more metal acid salt may also serve as a preservative, such as sodium/calcium/potassium benzoates, acetates, etc.

In another form, the compressed tobacco products disclosed herein can also optionally include a sugar alcohol, such as sorbitol, mannitol, xylitol or mixtures thereof. As may be appreciated, sugar alcohols can serve the dual purposes of a sweetener and a binder.

The compressed tobacco product formulation preferably contains amounts of tobacco, binder, glidant and optionally flavorants which provide a balance between desired mechanical properties (such as compressibility) and desired organoleptic properties (such as its taste, dissolvability, mouthfeel).

In one form, the formulation for the compressed tobacco product 10 includes about 30 to 50% by weight tobacco component, about 3 to 35% by weight filler-binder and less than about 1% by weight of lubricants and glidants. Sweeteners may be present in an amount of about 1 to about 3% by weight. The flavorant can be added in an effective amount to provide the desired flavoring; such as an amount ranging from about 1 wt. % to about 15 wt. % or about 3 wt. % to about 6 wt. %.

In another form, the amount of tobacco is about 40% by weight to impart a desired tobacco flavor.

In another form, the tobacco component comprises ground or powdered tobacco and/or optionally a tobacco extract. The tobacco component may include its own tobacco flavorants (flavor enhancers), but preferably, flavors are added separately as one or more discrete ingredients of the composition.

The compressed tobacco products may be manufactured by a direct compression process or by a granulation process. Both of these processes generate a compressed tobacco product which can, in an alternative form, be further processed to add a coating that may contain cellulose-based polymers, colorants, flavorants, or the like.

The steps involved in the manufacture of compressed tobacco products by a direct compression process include a dry blend tobacco blending and processing step, one or more blending steps, and a pressing step. In one form, a lipid infusion step is also employed. In an alternative form, the compressed tobacco product is further processed and a coating is added in a two-step process; a coating step and a drying step.

The tobacco blending and processing step may be conducted as follows. First, a tobacco blend is formed. As indicated above, the tobacco may comprise a blend of Bright, Burley, Dark Air Cured and/or Oriental tobaccos, or a single variety of the aforementioned tobaccos may be used instead of a blend. The tobacco may be cured or uncured; however, cured tobacco is preferred. The tobacco component may include tobacco laminae and/or stem, and may include ground improved stem.

Next, the tobacco blend is further processed through the use of a grinding step. The ground tobacco may have an average particle size of less than about 1 mm or less than about 0.5 mm or less than about 0.1 mm. In one form, the average particle size may be greater than about 100 nanometers or greater than about 1 micron. In another form, the average particle size may be between about 1 micron and about 0.1 mm (e.g., 400 mesh tobacco dust, wherein 95% of the particles pass through a mesh of 400 wires per square inch).

After the grinding step, the tobacco component may be cooked (semi-pasteurized) by any suitable technique. For example, the tobacco component can be cooked by high pressure, heat and/or steam. In one form, the cooking step is conducted at temperature of about 170 to about 190° F., for a period of about 1 to about 2 hours. Other cooking techniques can also be used. Following cooking, the tobacco component may be stored at or about room temperature until needed. In one form, lipid infusion is achieved by forming a mixture comprising powdered tobacco laminae and at least one lipid, prior to the cooking step and cooking the mixture of powdered tobacco laminae and the at least one lipid. An optional pH agent may be added to the mixture prior to the cooking step. The cooked mixture may then be used in the initial formulation of components described hereinbelow.

In one form, the tobacco component is dry blended with an initial formulation of components, including at least one filler-binder, at least one flavorant, at least one lubricant and at least one glidant. In another form, the at least one filler/binder, such as a microcrystalline cellulose or other material described hereinabove, the desiccant, such as silicon dioxide or fumed colloidal silica, the glidant, such as a fumed colloidal silica, and the at least one flavorant are added to an initial formulation in a first blending step, with the at least one lubricant added to the formulation in a second blending step. The amount of fumed colloidal silica added to the compressed tobacco product is sufficient to ensure that it will comprise between about 0.1% to about 5%, or about 0.2% to about 2%, or about 0.25% to about 0.5%, of the dry weight of the compressed tobacco product.

Optionally, after blending, the formulation may be milled using conventional techniques and machinery. In alternative forms, the formulation is milled through a 20-mesh or a 30-mesh screen using commercially available milling equipment such as, e.g., Quadro® or Comil®, available from Quadro Engineering of Millburn, N.J.

Figure 1B:
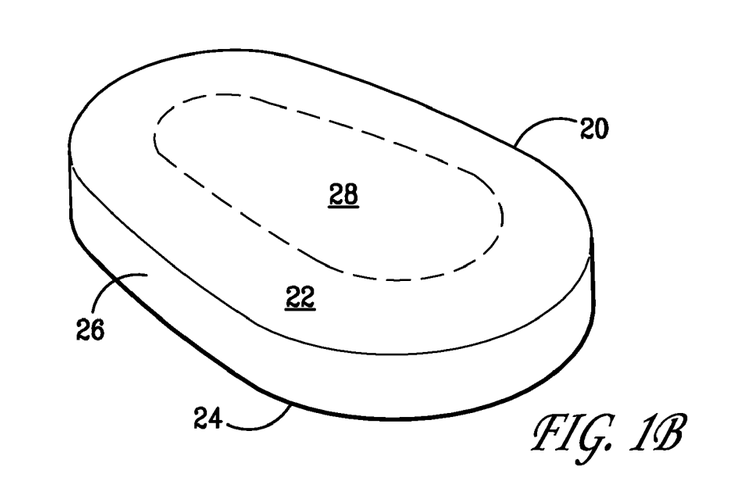
FIG. 1B is a perspective view of a compressed tobacco product in the form of an almond-shaped tablet.
Figure 2:
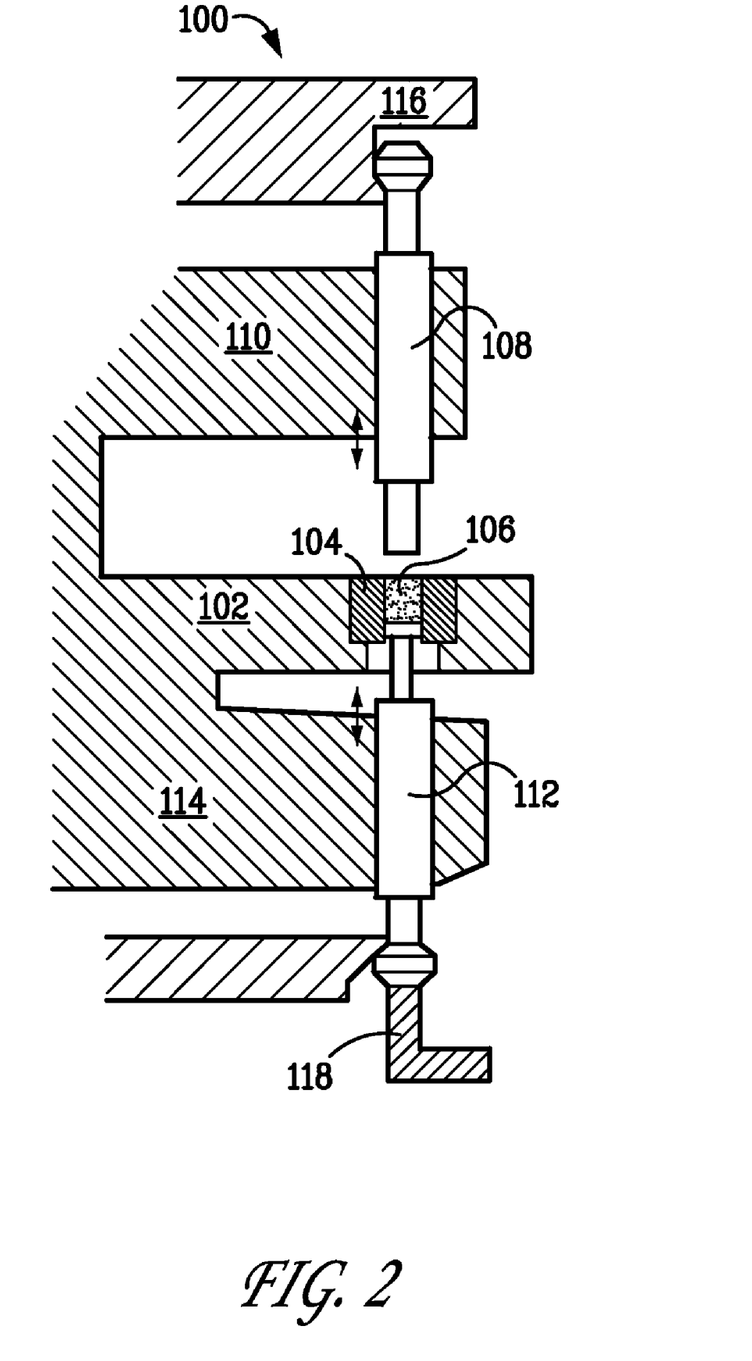
FIG. 2 is a schematic view of an apparatus for forming a dissolvable compressed tobacco product.

Referring now to FIG. 1B, another exemplary dissolvable compressed tobacco product 20 is shown that is adapted to be consumed orally and formed from a composition that includes a tobacco component, at least one flavorant, at least one sweetener, at least one filler-binder, at least one lubricant; at least one desiccant and a glidant. Other optional components may be employed, such as the inclusion of at least one lipid, as has been described hereinabove. Compressed tobacco product 20 includes at least a first surface 22, a second surface 24 and a side surface 26. One or more of these surfaces may optionally be coated, treated, embossed or debossed, as has been described. First surface 22 also includes a substantially concave surface portion 28, which as may be appreciated, increases the surface area of first surface 22. Second surface 26 may also include a substantially concave surface portion (not shown). Compressed tobacco product 20 may be provided with rounded edges, as shown, to improve friability and user comfort during consumption.

Figure 1C:
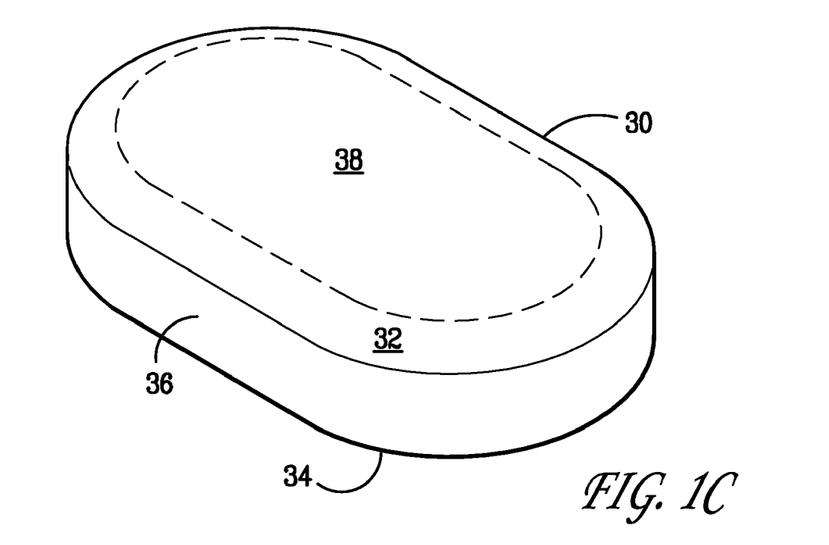
FIG. 1C is a perspective view of a compressed tobacco product in the form of a rectangular tablet.
Figure 1D:
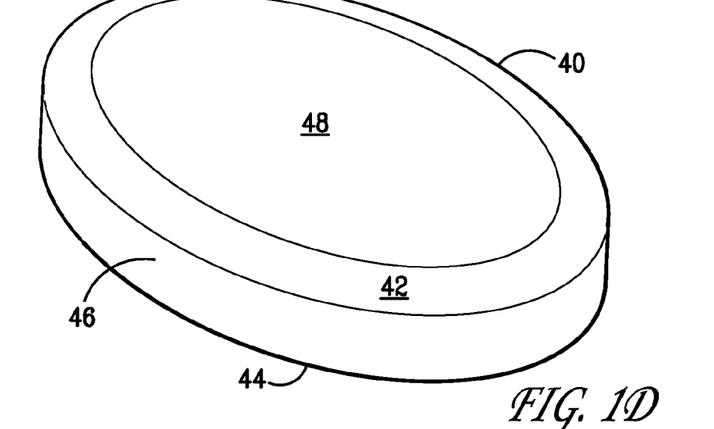
FIG. 1D is a perspective view of a compressed tobacco product in the form of a oval-shaped tablet.

Referring now to FIG. 1C, another exemplary dissolvable compressed tobacco product 30 is shown. Compressed tobacco product 30 includes at least a first surface 32, a second surface 34 and a side surface 36. First surface 32 also includes a substantially concave surface portion 38, which as may be appreciated, increases the surface area of first surface 32. Second surface 36 may also include a substantially concave surface portion (not shown). Once again, compressed tobacco product 30 may be provided with rounded edges, as shown, to improve friability and user comfort during consumption. FIG. 1D presents another exemplary dissolvable compressed tobacco product 40. Compressed tobacco product 40 includes at least a first surface 42, a second surface 44 and a side surface 46. First surface 42 also includes a substantially concave surface portion 48, which as may be appreciated, increases the surface area of first surface 42. Second surface 46 may also include a substantially concave surface portion (not shown). Compressed tobacco product 40 may be provided with rounded edges, as shown, to improve friability and user comfort during consumption.

Figure 1E:
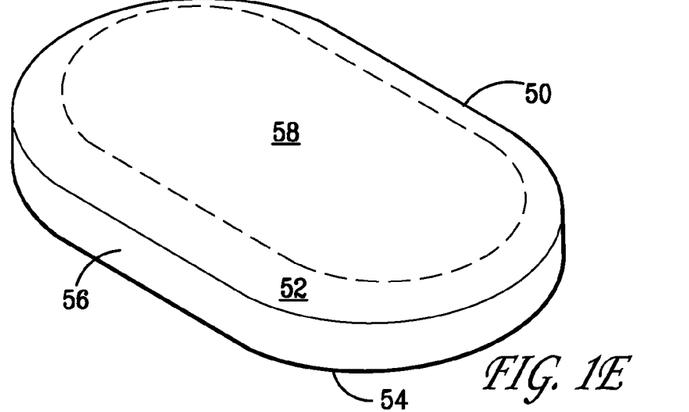
FIG. 1E is a perspective view of a compressed tobacco product in the form of a capsule-shaped tablet.
Figure 1F:
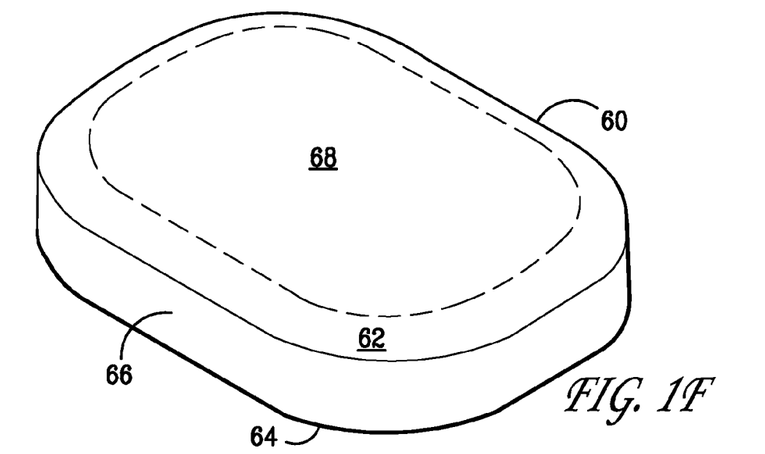
FIG. 1F is a perspective view of a compressed tobacco product in another form of rectangular tablet.

Referring now to FIG. 1E, another exemplary dissolvable compressed tobacco product 50 is shown. Compressed tobacco product 50 includes at least a first surface 52, a second surface 54 and a side surface 56. First surface 52 also includes a substantially concave surface portion 58, which as may be appreciated, increases the surface area of first surface 52. Second surface 56 may also include a substantially concave surface portion (not shown). Compressed tobacco product 50 may be provided with rounded edges, as shown, to improve friability and user comfort during consumption. FIG. 1F presents another exemplary dissolvable compressed tobacco product 60. Compressed tobacco product 60 includes at least a first surface 62, a second surface 64 and a side surface 66. First surface 62 also includes a substantially concave surface portion 68, which as may be appreciated, increases the surface area of first surface 62. Second surface 66 may also include a substantially concave surface portion (not shown). Compressed tobacco product 60 may be provided with rounded edges, as shown, to improve friability and user comfort during consumption.

Upon reaching the final formulation, the pressing or compression of the formulation is accomplished using a tablet press. Referring now to FIG. 2, a schematic of an exemplary tablet press 100 is shown. A die bore 106 is formed in a die 104 attached to a die table 102. A lower punch 112 is located within lower section, 114, below die bore 106. Lower punch 112 may be adjusted so that the volume of the die bore 106 is set at a predetermined volume for producing compressed tobacco products 10 (see FIG. 1) of desired size and weight. In one form, the compressed tobacco product has a weight of between about 200 to about 500 mg. In another form, the compressed tobacco product has a weight of about 300 mg.

The compressed tobacco product formulation may be fed through feed tube 118 and placed within die bore 106 and compressed with an upper punch 108, located within upper section 110, to form a compressed tobacco product 10. After compression, the compressed tobacco product 10 is pushed up by lower punch 112 so that the compressed tobacco product 10 is taken out from die bore 106. The compression force is applied by force application member 116 and may be about 1 to about 100 kN/punch, or about 5 to about 90 kN/punch, or about 8 to about 80 kN/punch.

The inner diameter of the die is usually about 3 to about 20 mm, or about 3 to about 13 mm, or about 4 to about 10 mm. The shape of die bore 106 of die 104 may be circular, oval, oblong, round, cylindrical, triangular, and the like. The top or lower surface of compressed tobacco product 10 can be embossed or debossed with a symbol or letters or any other suitable shape, as those skilled in the art will readily recognize.

While exemplary tablet press 100 is shown having a single die and punch arrangement, many alternative means to effect the compression step are available, and this disclosure is not intended to be limited by the use of any particular equipment. In another form, the compression step is carried out using a rotary type tablet press (not shown). The rotary type tableting machine has a rotary board with multiple dies, for forming tablet compressed tobacco product. As with the form depicted by FIG. 2, the compressed tobacco product formulation is inserted into the die and is subsequently press-molded.

The pre-compression and compression forces can be selected based on the type and model of the press, what physical properties are desired for the compressed tobacco product (e.g., desired, hardness, friability, disintegration or dissolution characteristics, etc.), the desired appearance and size of the compressed tobacco product, and the like. Once again, the compression force may be about 1 to about 100 kN/punch, or about 5 to about 90 kN/punch, or about 8 to about 80 kN/punch. The compressed tobacco product 10 produces by the compression step may have a hardness of about 20 N to about 200 N, or about 50 N to about 150 N. In other forms, the tablet can buccally dissolve within at least about 30 minutes or at least about 15 minutes or at least 10 minutes.

In one form, following the pressing operation, the compressed tobacco product may be placed in an oil bath containing a hot lipid mixture. The hot liquid lipid fills the interstitial spaces of the tablet, extracting oil soluble materials from the tobacco matrix and incorporating them into the lipid. In this manner, the lipid impregnates or infuses the compressed tobacco matrix with the hot lipid mixture. The oil bath is maintained at a temperature of about 40 to about 80° C., or about 50 to about 70° C., or about 55 to about 65° C. The compressed tobacco product remains in the oil bath for a period of about 5 to about 25 minutes, or from about 10 to about 20 minutes, in order to achieve a proper level of lipid infusion. The oil bath temperature and the time that the compressed tobacco product spends in the oil bath is also a function, in part, of the slip melting point of the lipid employed. The oil bath can be a true immersion or can also be applied via spray application in a rotary coater or via vacuum/pressure vessels. The application can be inert gas purged to remove the potential for lipid oxidation if substantially unsaturated oils are used.

Following the infusion step, the compressed tobacco product is subjected to a heating step to allow the liquefied lipids to be deposited evenly in the tablet interstices via capillary action. Heating may be achieved in a number of ways. In one form, the heating step is conducted in an oven maintained at a temperature of about 30 to about 70° C., or about 40 to about 60° C., or about 45 to about 55° C. The compressed tobacco product remains in the oven for a period of about 5 to about 25 minutes, or from about 10 to about 20 minutes, in order to achieve a low level of moisture (less than about 5%). Following the oven heating step, the compressed tobacco product is allowed to cool. In another form, the heating step is skipped and the post-infusion cooling is conducted at room temperature. When cooled in this manner, this lipid mix does not penetrate as deeply and instead forms an attractive, thin, smooth, shell on the surface of the tobacco matrix.

In another form, heating is accomplished through the use of a fluid bed dryer. In fluid bed drying, a hot air stream is introduced at the base of a product container filled with the compressed tobacco product. A draft is created by means of a blower and fresh air is sucked into the unit. This hot air stream expands the material at a certain velocity, creating turbulence in the product. The phenomenon is known as fluidization and produces agitation of the compressed tobacco product by hot air. Heat transfer is relatively high and uniform. A fluid bed dryer may be obtained from Riddhi Pharma Machinery Limited of Maharashtra, India, and other sources. Following the fluid bed drying step, the compressed tobacco product is allowed to cool. When cooled, this lipid mix also forms an attractive, thin, smooth, shell on the surface of the tobacco matrix.

As the tablet cools and the lipids solidify, the dissolved materials remain with the now solid lipid until the compressed tobacco product is placed in the mouth. Once in the mouth, the lipids melt, allowing the dissolved flavors to exit the compressed tobacco product still in the liquid lipid which then coats the tongue and oral mucosa, providing a pleasant and smooth mouth feel. The hydrophobic lipid also inhibits migration of saliva into the interior of the tablet, smoothing dissolution and reducing the spalling of the tobacco matrix and resulting muddy texture of a conventional compressed tobacco product. Additionally, many flavors and aromas are hydrophobic and thus difficult to liberate from a conventional compressed tobacco product using only aqueous saliva dissolution. Instead, the oils allow these flavors and aromas to be spread easily within the mouth and retronasal olfactory environment. Hydrophobic flavor oils may be added directly to the infusion lipid blend or sprayed on post infusion.

In other forms, lipid matrices may be added after compression, as a simple coating, using a heated pan coater, via spraying, via cascade enrober enrobement. Tobacco solids and/or flavors can be added to the coating lipids to form an easily melted-in-mouth tobacco flavored shell. The lipid coating can be coated with a thin quick dissolve material such as sugars and/or soluble starches to protect the lipid coat from melting at high storage temperatures.

The steps involved in the manufacture of a compressed tobacco product by a granulation process include a blending step, a granulation step, a drying step, an optional blending step and a compression step. Other optional steps may be employed, such as an infusion step to infuse at least one lipid, as has been described hereinabove. In another form, the compressed tobacco product is further processed and a coating added in a two-step process; a coating step and a drying step.

In the granulation manufacturing process, a tobacco blend is first formed. As indicated above, the tobacco may comprise a blend of Bright, Burley and/or Oriental tobaccos, or a single variety of the aforementioned tobaccos may be used instead of a blend. The tobacco may be cured or uncured; however, cured tobacco is preferred. The tobacco component may include tobacco laminae and/or stem.

Next, the tobacco blend is further processed through the use of a grinding step. The ground tobacco may have an average particle size of less than about 1 mm or less than about 0.5 mm or less than about 0.1 mm. In one form, the average particle size may be greater than about 100 nanometers or greater than about 1 micron. In another form, the average particle size may be between about 1 micron and about 0.1 mm (e.g., 400 mesh tobacco dust, wherein 95% of the particles pass through a mesh of 400 wires per square inch).

Following the grinding step, the initial mixture is then granulated. The mixture for use in granulation can be formed by combining the tobacco components together with a suitable liquid in a container such as a mixing vessel. A preferred liquid is water, although a mixture of liquids such as water and alcohol (ethanol) can be used. Where the tobacco component comprises ground or powdered tobacco, some compounds from the tobacco may be expected to go into solution. In one form, the mixing vessel is temperature controlled. The aqueous solution may also include at least about 0.5% cellulose-based polymer. This blending process is commonly called wet granulation. As may be appreciated by those skilled in the art, granulation is commonly defined as a size-enlargement process wherein small particles are gathered into larger, permanent aggregates in which the original particles can still be identified. Wet granulation is a variation on this process and refers to a granulation that adds solvents and binders to the enlargement process. For more information, see Lipps (1993) *J. Pharm. Sci.* 83:937-947; or Olmo (1998) *Drug Dev. Ind. Pharm.* 24:771-778.

A variety of such blending, or mixing, or granulating, apparatus are commonly available. For example, the granulation can be done on a fluid bed granulator, such as one available from Glatt Air Techniques Inc. of Ramsey, N.J.

The temperature during granulation can be set at any point as long as it does not exceed the melting point of any components in the formulation and the balance between spraying and drying is maintained. In one form, the temperature during granulation and drying is at a relatively low heat setting, i.e., a range of about 20° C. to about 50° C. The formulation, once granulated, is dried until the temperature reaches 40° C. before forming the compressed tobacco product.

Next, the tobacco can be cooked by any suitable technique. For example, the tobacco component can be pasteurized by high pressure, heat and/or steam. In one form, the cooking step is conducted at a temperature of about 170 to about 190° F., for a period of about 1 to about 2 hours. Other pasteurizing techniques can also be used. Following cooking, the tobacco component may be stored at or about room temperature until needed. In one form, lipid infusion is achieved by forming a mixture comprising powdered tobacco laminae and at least one lipid, prior to the cooking step and cooking the mixture of powdered tobacco laminae and the at least one lipid. An optional pH agent may be added to the mixture prior to the cooking step. The cooked mixture may then be used in the initial formulation of components described hereinbelow.

Following the granulation step, the tobacco component is dry blended with an initial formulation of components, including at least one filler-binder, at least one flavorant, at least one lubricant and at least one glidant. In another form, the at least one filler/binder, such as a microcrystalline cellulose or other material described hereinabove, the glidant, such as a fumed colloidal silica, and the at least one flavorant are added to an initial formulation in a first blending step, with the at least one lubricant added to the formulation in a second blending step. The amount of fumed colloidal silica added to the compressed tobacco product is sufficient to ensure that it will comprise between about 0.1% to about 5%, or about 0.2% to about 2%, or about 0.25% to about 0.5%, of the dry weight of the compressed tobacco product.

Optionally, after blending, the formulation may be milled using conventional techniques and machinery. In alternative forms, the formulation may be milled through a 20-mesh or a 30-mesh screen using commercially available milling equipment such as, e.g., Quadro® or Comil®, available from Quadro Engineering of Millburn, N.J.

Upon reaching the final formulation, the pressing or compression of the formulation is accomplished, once again, using a tablet press 100 of the type depicted in FIG. 2. Referring again to FIG. 2, a die bore 106 is formed in a die 104 attached to a die table 102. A lower punch 112 is located within lower section 114, below die bore 106. Lower punch 112 may be adjusted so that the volume of the die bore 106 is set at a predetermined volume for producing compressed tobacco products 10 (see FIG. 1) of desired size and weight. In one form, the compressed tobacco product has a weight of between about 200 to about 500 mg. In another form, the compressed tobacco product has a weight of about 300 mg.

The compressed tobacco product formulation may be fed through feed tube 118 and placed within die bore 106 and compressed with an upper punch 108, located within upper section 110, to form a compressed tobacco product 10. After compression, the compressed tobacco product 10 is pushed up by lower punch 112 so that the compressed tobacco product 10 is taken out from die bore 106. The compression force is applied by force application member 116 and may be about 1 to about 100 kN/punch, or about 5 to about 90 kN/punch, or about 8 to about 80 kN/punch.

The inner diameter of the die is usually about 3 to about 20 mm, or about 3 to about 13 mm, or about 4 to about 10 mm. The shape of die bore 106 of die 104 may be circular, oval, oblong, round, cylindrical, triangular, and the like. The top or lower surface of compressed tobacco product 10 can be embossed or debossed with a symbol or letters or any other suitable shape.

While exemplary tablet press 100 is shown having a single die and punch arrangement, many alternative means to effect the compression step are available, and this disclosure is not intended to be limited by the use of any particular equipment. In another form, the compression step is carried out using a rotary type tablet press (not shown). The rotary type tableting machine has a rotary board with multiple dies, for forming tablet compressed tobacco product.

The compression force can be selected based on the type and model of the press, what physical properties are desired for the compressed tobacco product (e.g., desired, hardness, friability, disintegration or dissolution characteristics, etc.), the desired appearance and size of the compressed tobacco product, and the like. Once again, the compression force may be about 1 to about 100 kN/punch, or about 5 to about 90 kN/punch, or about 8 to about 80 kN/punch. The compressed tobacco product 10 produced by the compression step may have a hardness of about 20 N to about 200 N, or about 50 N to about 150 N. In other forms, the tablet can buccally dissolve within at least about 30 minutes or at least about 15 minutes or at least 10 minutes.

As described hereinabove, following the pressing operation, the compressed tobacco product may be placed in an oil bath containing the hot lipid mixture. The hot liquid lipid fills the interstitial spaces of the tablet, extracting oil soluble materials from the tobacco matrix and incorporating them into the lipid. In this manner, the lipid impregnates or infuses the compressed tobacco product matrix with the hot lipid mixture. The oil bath is maintained at a temperature of about 40 to about 80° C., or about 50 to about 70° C., or about 55 to about 65° C. The compressed tobacco product remains in the oil bath for a period of about 5 to about 25 minutes, or from about 10 to about 20 minutes, in order to achieve a proper level of lipid infusion. The oil bath temperature and the time that the compressed tobacco product spends in the oil bath is also a function, in part, of the slip melting point of the lipid employed.

Following the infusion step, the compressed tobacco product is subjected to a heating step. Heating may be achieved in a number of ways. In one form, the heating step is conducted in an oven maintained at a temperature of about 30 to about 70° C., or about 40 to about 60° C., or about 45 to about 55° C. The compressed tobacco product remains in the oven for a period of about 5 to about 25 minutes, or from about 10 to about 20 minutes, in order to achieve a low level of moisture (less than about 5%). Following the oven heating step, the compressed tobacco product is allowed to cool. In another form, there is no heating and the hot lipid infused tablet is cooled at room temperature. When cooled in this manner, this lipid mixture also forms an attractive, thin, smooth, shell on the surface of the tobacco matrix.

In another form, heating is accomplished through the use of a fluid bed dryer. In fluid bed heating, a hot air stream is introduced at the base of a product container filled with the compressed tobacco product. A draft is created by means of a blower and fresh air is sucked into the unit. This hot air stream expands the material at a certain velocity, creating turbulence in the product. The phenomenon is known as fluidization and produces agitation of the compressed tobacco product by hot air. Heat transfer is relatively high and uniform. A fluid bed dryer may be obtained from Riddhi Pharma Machinery Limited of Maharashtra, India, and other sources. Following the fluid bed heating step, the compressed tobacco product is allowed to cool. When cooled, this lipid mix also forms an attractive, thin, smooth, shell on the surface of the tobacco matrix.

As the tablet cools and the lipids solidify, the dissolved materials remain with the now solid lipid until the compressed tobacco product is placed in the mouth. Once in the mouth, the lipids melt, allowing the dissolved flavors to exit the compressed tobacco product still in the liquid lipid which then coats the tongue and oral mucosa, providing a pleasant and smooth mouth feel. The hydrophobic lipid also inhibits migration of saliva into the interior of the tablet, smoothing dissolution and reducing the spalling of the tobacco matrix and resulting muddy texture of a conventional compressed tobacco product. Additionally, many flavors and aromas are hydrophobic and thus difficult to liberate from a conventional compressed tobacco product using only aqueous saliva dissolution. Instead, the oils allow these flavors and aromas to be spread easily within the mouth and retronasal olfactory environment, In other forms, lipid matrices may be added after compression, as a coating, using a heated pan coater, via spraying, via cascade enrobement. This coating may or may not contain tobacco solids and/or flavors. The lipid coating can be coated with a thin quick dissolve material such as sugars and/or soluble starches to protect the lipid coat from melting at high storage temperatures As indicated above, in one form, the compressed tobacco products made either by the granulation or the direct compression manufacturing processes may be coated. Coating of the compressed tobacco product is the final step prior to packaging. As may be appreciated, coating the compressed tobacco products disclosed herein can provide a moisture barrier, prevent de-dusting of the product improve physical appearance, maintain integrity, improve friability and potentially increase overall hardness. A commercially available pan coater may be used to spray a fine mist of an aqueous coating solution on a tumbling bed of compressed tobacco products at a controlled rate The coating process disclosed herein includes the steps of coating the compressed tobacco products with an aqueous dispersion comprising a cellulose-based polymer; followed by drying the coated compressed tobacco products, wherein the drying does not heat the tablet more than about 40° C.

The coating solution can contain a variety of ingredients, including flavorants, colorants, sweeteners and the like. For example, in one form, the compressed tobacco product may be coated with an aqueous dispersion of hydroxypropyl methylcellulose, polyethylene glycol, titanium dioxide, and a colorant. In another form, the compressed tobacco product is coated with an aqueous dispersion of hydroxypropyl methylcellulose, polyethylene glycol, and maltodextrin. In another form, the coating material may be an edible polysaccharide. Conventional equipment may be used in the coating process; see, e.g., Sastry (1998) *Pharm Dev Technol.* 3:423-432; Parikh (1993) *Pharm Res.* 10:525-534.

In one form, the coating solution is prepared by adding three food grade ingredients to de-ionized water, and stirring the solution at ambient temperature for 20 minutes to 2 hours. The base ingredient hydroxypropyl methyl cellulose is mixed with a plasticizer, such as glycerine or triacetin, and an aqueous solution of polymer shellac. The polymer shellac provides the moisture barrier properties. The film coating adds between 0.5% to 10% to the weight of the compressed tobacco products.

In another form, the compressed tobacco products disclosed herein can be provided with a hard outer shell coating applied using a pan coating process. As may be appreciated, in this process, the compressed tobacco products are tumbled in a pan or other device while the coating material is applied slowly thereto. As the pan rotates a hard shell of coating forms on the exterior of the compressed tobacco product. In the same process or another panning operation, wax or a polishing agent may be put in the pan with the compressed tobacco products to give them an attractive luster. The rotation of the pan can also help develop the finished shape of the compressed tobacco products.

The compressed tobacco products are sized and shaped to be place within a buccal cavity and consumed orally. The compressed tobacco products can have a diameter of from about 2 mm to about 30 mm. The compressed tobacco products are adapted to dissolve completely, in less than about 90 minutes, or in less than about 15 minutes, or in less than about 10 minutes. The compressed tobacco products are adapted to be entirely consumed.

According to a further embodiment, the compressed tobacco products can comprise two or more layers, wherein adjacent layers are bonded (e.g., laminated) together to form a unitary compressed tobacco product. Each layer in a multi-layer compressed tobacco product can be substantially the same. In another form, the two or more layers in a multi-layer compressed tobacco product can be substantially different. For example, the thickness and composition (e.g., amount, distribution and/or kind of tobacco component) in each layer in a multi-layer compressed tobacco product can be different. These parameters can be varied to provide, e.g., different rates of dissolution, different flavors or combinations of flavors, different mouth feels, or combinations of these, for each layer. By varying the composition and properties of each layer, the consumer's experience can vary in a pleasing fashion.

One method of forming the compressed tobacco product from laminated layers is placing the layers into contact with each other while at least one surface of at least one of the layers has not yet fully dried. Alternatively, two or more formed and dried layers can be adhered together by introducing between their respective opposing surfaces a binding agent, which adheres to both of the opposing surfaces and binds them together. This binding agent may be an edible material, containing one or more of the same components used to form the compressed tobacco product, or a water soluble polysaccharide. The material may be applied by any suitable technique, e.g., by spray coating, or the like.

In yet another form, the compressed tobacco products can be placed within a chewable or dissolvable pouch. The pouch provides sufficient flexibility to obtain a variety of different products. For example, the pouch can be relatively fast dissolving in the mouth, while the compressed tobacco product can be slower dissolving, or may contain flavorants different from those contained in the pouch material. As may be appreciated, the result is that the consumer perceives different sensory experiences at different times during consumption of the product, or that the sensory experiences provided by the dissolution of the different components results in sensory experiences not obtainable from consumption of each component individually.

As may be appreciated, the compositions and processes employed to form the compressed tobacco products disclosed herein must be designed to perform in three distinct modes: 1) a production mode; 2) a tablet mode; and 3) a consumer use and enjoyment mode. It has been discovered that certain composition ingredients and/or process steps, while beneficially affected one mode, may positively or negatively affect another mode, as will be described in more detail hereinbelow.

In the formulation of the tobacco blend, the use of ground improved stem provides a higher level of cellulose to the compressed tobacco product. A higher level of cellulose improves the production mode, as it is beneficial to making a tablet, and, while it produces a product with a more "mushy" feel, it improves the consumer use and enjoyment mode, as it produces particles that more readily pass down the throat of a consumer. The use of the highly flavorful dark air cured tobacco in the tobacco blend permits a higher level of ground improved stem to be employed, while still providing a high level of enjoyment.

In the binder system, the use of microcrystalline cellulose, as an effective binder, improves the production mode, while also improving the tablet mode, as it improves tablet hardness. However, the use of microcrystalline cellulose at too high a level can negatively impact the consumer use and enjoyment mode, as it increases grittiness on dissolution. The use of xanthan gum provides a number of benefits. First, as an effective binder, it improves the production and tablet modes.

Second, it controls the release of extractables, which benefits the consumer use and enjoyment mode. Finally, it serves as a moisture carrier, which benefits all three modes.

Another binder system agent, maltodextrin, also benefits all three modes. First, as an effective binder, it improves the production mode. Second, it improves product hardness, benefitting the tablet mode. Third, it improves product texture, reduces sliminess and provides an improved mouth feel, benefitting the consumer use and enjoyment mode.

Pre-gelatinized corn starch, another binder system component, benefits the production mode, may play a role in product coating, but can produce a slimy mouth feel, negatively affecting the consumer use and enjoyment mode. Corn starch, such as FloMax 8®, behaves very differently, improving product hardness and, thus, the tablet mode.

Sweeteners are employed for their impact on the consumer use and enjoyment mode. Sucrasweet® and sucralose have been found to benefit consumer use and enjoyment. Although sugar alcohols have been found to provide adequate sweetness, they also serve as a quick release agent with respect to extractables and, as such, serve to negatively impact consumer use and enjoyment. Additionally, sugar alcohols have been found to negatively affect product hardness, thus also affecting the tablet mode.

Lubricants are employed to benefit the production mode. While magnesium stearate is an effective lubricant, if used at too high a level, it can reduce product hardness and negatively impact the tablet mode. As mentioned hereinabove, the use of fumed colloidal silica can serve three important purposes simultaneously. First, it is an effective lubricant, benefiting the production mode. Second, it serves a desiccant, improving the production and tablet modes. As a desiccant, the fumed colloidal silica counteracts the tendency of the finely ground tobacco to absorb moisture. Third, it serves as a glidant, benefiting the production and consumer use and enjoyment modes.

Flavor and aroma agents may be employed to benefit the consumer use and enjoyment mode. Flavor and aroma agents suitable for use herein are essential oils, naturally ground coffee, tea, cacao, and mint and essences of coffee, tea, cacao, and mint.

It has been observed that several finished product properties, including dissolving and flavor characteristics may be influenced by controlling the following variables: 1) porosity of the tablet, 2) tobacco particle size distribution, 3) particle size distribution of the other ingredients, 4) period of time that the compressed tobacco product spends in the lipid oil bath, 5) lipid oil bath temperature, 6) slip melting temperature of the lipid or lipid mixtures, 7) level of lipid inclusion, 8) compressed tobacco product drying temperature, and 9) the interaction and/or combination of these parameters. Additionally, it has been observed that the porosity of the compressed tobacco product tablet and, thus, lipid inclusion level, may be controlled by compression pressure and/or tablet composition or a combination of both approaches. Additional tablet attributes may be obtained by adding flavor, sweeteners, warming agents, cooling agents, gas release matrices. and/or a combination of some or all ingredients. Additional overcoats such as waxes, sugars, sugar alcohols, proteins, polysaccharides. oligosaccharides. etc can be added to prevent the escape of the lipids during high temperatures in storage.

Product testing has shown that a lipid-infused compressed tobacco product yields improves flavor and texture attributes: Additionally, cleaner, smoother dissolving characteristics are achieved in the mouth. Other benefits include improved delivery of hydrophobic flavors and aroma, and reduced throat burn and irritation. Finally, as described above, the lipid-infused compressed tobacco products described herein have an attractive appearance, both from the standpoint of color and visual texture All patents, test procedures, and other documents cited herein, including priority documents, are fully incorporated by reference to the extent such disclosure is not inconsistent with this disclosure and for all jurisdictions in which such incorporation is permitted.

While the illustrative embodiments disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which the disclosure pertains.

What is claimed is:

1. A method of making a dissolvable compressed tobacco product comprising the steps of:
   (a) forming a mixture of a tobacco component, at least one flavorant, at least one filler-binder; at least one lubricant; and at least one glidant;
   (b) compressing the mixture into a die to form a compressed tobacco product; and
   (c) infusing the compressed tobacco product with at least one lipid,
   wherein the step of infusing the compressed tobacco product with at least one lipid comprises: (i) placing the compressed tobacco product in an oil bath containing the at least one lipid; (ii) filling interstitial spaces of the compressed tobacco product with the at least one lipid; and (iii) heating the compressed tobacco product.

2. The method of claim 1, wherein the at least one lipid is selected from tropical oils, butters, vegetable oils, shortenings and sucrose polyesters.

3. The method of claim 1, wherein the at least one lipid comprises palm oil.

4. The method of claim 3, wherein the palm oil comprises palm kernel oil that has been refined, bleached, hydrogenated, and deodorized.

5. The method of claim 3, wherein the palm oil has a slip melting point of about 96 to about 104° F.

6. The method of claim 1, further comprising the step of forming a shell coating comprising at least one lipid on a surface of the compressed tobacco product.

7. The method of claim 1, wherein the oil bath is maintained at a temperature of about 40 to about 80° C.

8. The method of claim 1, wherein the oil bath is maintained at a temperature of about 50 to about 70° C.

9. The method of claim 1, wherein the compressed tobacco product remains in the oil bath for a period of about 5 to about 25 minutes.

10. The method of claim 1, wherein the compressed tobacco product remains in the oil bath for a period of about 10 to about 20 minutes.

11. The method of claim 1, wherein said heating step is conducted in an oven maintained at a temperature of about 30 to about 70° C.

12. The method of claim 1, wherein said heating step is conducted in an oven maintained at a temperature of about 40 to about 60° C.

13. The method of claim 1, wherein said heating step is conducted at room temperature.

14. The method of claim 1, wherein said heating step is conducted in a fluid bed dryer.

15. The method of claim 1, wherein the mixture further comprises a pH agent.

16. The method of claim 1, wherein the composition comprises from about 30% to about 50% by weight of said tobacco component.

17. The method of claim 16, wherein the composition comprises up to about 40% by weight of said tobacco component.

18. The method of claim 1, wherein the at least one tobacco component comprises ground or powdered tobacco with an average particle size of between about 100 nm and 1 mm.

19. The method of claim 1, wherein the at least one tobacco component comprises ground or powdered tobacco.

20. The method of claim 1, wherein the composition comprises includes a flavorant in an amount of up to 15% by weight flavorant.

21. The method of claim 20, wherein the flavorant comprises peppermint, tea, cocoa, spices, almond, vanilla, rum, amaretto, brandy or mixtures thereof.

22. The method of claim 1, wherein the composition comprises from about 5 to about 35% by weight binder.

23. The method of claim 1, wherein said binder comprises a microcrystalline cellulose, a sprayed processed lactose, a dicalcium phosphate dehydrate, a sprayed processed sucrose, a sprayed maltodextrin or mixtures thereof.

24. The method of claim 1, wherein said lubricant comprises a hydrophobic lubricant.

25. The method of claim 24, wherein said hydrophobic lubricant comprises magnesium stearate, calcium stearate, stearic acid, talc or mixtures thereof.

26. The method of claim 1, wherein said lubricant comprises a hydrophilic lubricant.

27. The method of claim 26, wherein said hydrophilic lubricant comprises DL leucine, sodium benzoate, polyethylene glycol or mixtures thereof.

28. The method of claim 1, wherein the composition comprises less than about 1% by weight glidant.

29. The method of claim 28, wherein the composition comprises from about 0.25% to about 0.5% by weight glidant.

30. The method of claim 1, wherein said glidant comprises fumed or colloidal silica.

31. The method of claim 1, further comprising a desiccant, wherein said desiccant comprises fumed or colloidal silica.

32. The method of claim 1, wherein said lubricant comprises fumed or colloidal silica.

33. The method of claim 1, wherein said compressed tobacco product is in the form of a tablet.

34. The method of claim 1, further comprising one or more additives selected from the group of sweeteners, fragrances, coloring agents and preservatives.

35. The method of claim 1, wherein the compressed tobacco product comprises 30 to 50% by weight tobacco component, 5 to 35% by weight binder and less than 1% by weight glidant.

36. The method of claim 1, wherein the mixture is prepared by forming a first aqueous mixture of the tobacco component and optional flavorant, forming a second aqueous mixture of the lubricant and binder, and combining the first and second mixtures.

* * * * *